United States Patent
Hopwood et al.

(12)

(10) Patent No.: US 6,200,563 B1
(45) Date of Patent: *Mar. 13, 2001

(54) SYNTHETIC MAMMALIAN SULPHAMIDASE AND GENETIC SEQUENCES ENCODING SAME

(75) Inventors: John Joseph Hopwood, Stonyfell (AU); Hamish Steele Scott, Geneva (CH); Craig Geoffrey Freeman, Rivett (AU); Charles Phillip Morris, Indooroopilly (AU); Lianne Cheryl Blanch, McMahons Pt (AU); Xiao Hui Guo, Camden PK. (AU)

(73) Assignee: Women's and Children's Hospital (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/370,867

(22) Filed: Aug. 9, 1999

Related U.S. Application Data

(60) Continuation of application No. 08/874,763, filed on Jun. 13, 1997, now Pat. No. 5,972,333, which is a division of application No. 08/424,881, filed on Apr. 19, 1995, now Pat. No. 5,863,782.

(51) Int. Cl.[7] .............................. A61K 38/46; C12N 9/96; C12N 9/14; C07H 21/04; C07K 1/00

(52) U.S. Cl. ..................... 424/94.6; 435/188; 435/195; 435/252.3; 435/320.1; 536/23.2; 530/350

(58) Field of Search .......................... 424/94.6; 435/195, 435/188, 252.3, 320.1; 536/23.2; 530/350

(56) References Cited

U.S. PATENT DOCUMENTS

| 5,298,395 | 3/1994 | Park | 435/7.21 |
|---|---|---|---|
| 5,972,333 | * 10/1999 | Hopwood et al. | 424/94.6 |

OTHER PUBLICATIONS

Alberts, et al. (1989) "DNA Cloning and Genetic Engineering", *The Molecular Biology of The Cell*, Second Edition, Chapter 5, Garland Publishing, Inc., New York, pp. 258–266.

Bielicki, J., et al. (1998) "Recombinant huan sulphamidase: expression, amplification, purification and characterization", *Biochem. J.* 329:145–150.

Coulter II, et al. (1993) "Identification of Cortexin: A Novel, Neuron–Specific, 82–Residue Membrane Protein Enriched in Rodent Cerebral Cortex", *Journal of Neurochemistry* 62(2): 756–759.

Dean, et al. (1973) "Mobilization of glycosaminoglycans by plasma infusion in mucopolysaccharidosis type III–two types of response", *Nature New Biology* 243:143–146.

Ford, et al. (1991) "Fusion tails for the recovery and purification of recombinant proteins", *Protein Expression and Purification* 2(2/3):95–107.

Freeman, et al. (1986) "Human Liver Sulphamate Sulphohydrolase", *Biochem. J.* 234:83–92.

Mahuran, et al. (1983) "A Rapid Four Column Purification of 2–Deoxy–D–Glucoside–2–Sulphamate Sulphohydrolase from Human Liver", *Biochimica et Biophysica Acta* 757:359–365.

O'Brien, et al. (1973) "Sanfilippo disease type B: enzyme replacement and metabolic correction in cultured fibroblasts", *Science* 181(101):753–755.

* cited by examiner

*Primary Examiner*—Tekchand Saidha
(74) *Attorney, Agent, or Firm*—Ann R. Pokalsky

(57) ABSTRACT

The present invention relates generally to mammalian sulphamidase and to genetic sequences encoding same and to the use of these in the investigation, diagnosis and treatment of subjects suspected of or suffering from sulphamidase deficiency.

5 Claims, 3 Drawing Sheets

FIG. 2A

```
                    M   S   C   P   V   P   A   C   C   A   L   L   L   V   L   G      16
GAATTCCGGGCCATGAGCTGCCCCGTGCCCGCCTGCTGCGCGCTGCTGCTAGTCCTGGGG              60

L   C   R   A ▼ R   P   R   N   A   L   L   L   A   D   D   G   G   F   E      36
CTCTGCCGGGCGCGTCCCCGGAACGCACTGCTGCTCCTCGCGGATGACGGAGGCTTTGAG             120
                 *

S   G   A   Y   N   N   S   A   I   A   T   P   H   L   D   A   L   A   R   R    56
AGTGGCGCGTACAACAACAGCGCCATCGCCACCCCGCACCTGGACGCCTTGGCCCGCCGC            180

S   L   L   F   R   N   A   F   T   S   V   S   S   C   S   P   S   R   A   S    76
AGCCTCCTCTTTCGCAATGCCTTCACCTCGGTCAGCAGCTGCTCTCCCAGCCGCGCCAGC            240

L   L   T   G   L   P   Q   H   Q   N   G   M   Y   G   L   H   Q   D   V   H    96
CTCCTCACTGGCCTGCCCCAGCATCAGAATGGGATGTACGGGCTGCACCAGGACGTGCAC            300

H   F   N   S   F   D   K   V   R   S   L   P   L   L   L   S   Q   A   G   V   116
CACTTCAACTCCTTCGACAAGGTGCGGAGCCTGCCGCTGCTGCTCAGCCAAGCTGGTGTG            360

R   T   G   I   I   G   K   K   H   V   G   P   E   T   V   Y   P   F   D   F   136
CGCACAGGCATCATCGGGAAGAAGCACGTGGGGCCGGAGACCGTGTACCCGTTTGACTTT            420
                                  *                                    *

A   Y   T   E   E   N   G   S   V   L   Q   V   G   R   N   I   T   R   I   K   156
GCGTACACGGAGGAGAATGGCTCCGTCCTCCAGGTGGGGCGGAACATCACTAGAATTAAG            480

L   L   V   R   K   F   L   Q   T   Q   D   D   R   P   F   F   L   Y   V   A   176
CTGCTCGTCCGGAAATTCCTGCAGACTCAGGATGACCGGCCTTTCTTCCTCTACGTCGCC            540

F   H   D   P   H   R   C   G   H   S   Q   P   Q   Y   G   T   F   C   E   K   196
TTCCACGACCCCCACCGCTGTGGGCACTCCCAGCCCCAGTACGGAACCTTCTGTGAGAAG            600

F   G   N   G   E   S   G   M   G   R   I   P   D   W   T   P   Q   A   Y   D   216
TTTGGCAACGGAGAGAGCGGCATGGGTCGTATCCCAGACTGGACCCCCCAGGCCTACGAC            660

P   L   D   V   L   V   P   Y   F   V   P   N   T   P   A   A   R   A   D   L   236
CCACTGGACGTGCTGGTGCCTTACTTCGTCCCCAACACCCCGGCAGCCCGAGCCGACCTG            720

A   A   Q   Y   T   T   V   G   R   M   D   Q   G   V   G   L   V   L   Q   E   256
GCCGCTCAGTACACCACCGTCGGCCGCATGGACCAAGGAGTTGGACTGGTGCTCCAGGAG            780
                                  *

L   R   D   A   G   V   L   N   D   T   L   V   I   F   T   S   D   N   G   I   276
CTGCGTGACGCCGGTGTCCTGAACGACACACTGGTGATCTTCACGTCCGACAACGGGATC            840

P   F   P   S   G   R   T   N   L   Y   W   P   G   T   A   E   P   L   L   V   296
CCCTTCCCCAGCGGCAGGACCAACCTGTACTGGCCGGGCACTGCTGAACCCTTACTGGTG            900

S   S   P   E   H   P   K   R   W   G   Q   V   S   E   A   Y   V   S   L   L   316
TCATCCCCGGAGCACCCAAAACGCTGGGGCCAAGTCAGCGAGGCCTACGTGAGCCTCCTA            960

D   L   T   P   T   I   L   D   W   F   S   I   P   Y   P   S   Y   A   I   F   336
GACCTCACGCCCACCATCTTGGATTGGTTCTCGATCCCGTACCCCAGCTACGCCATCTTT           1020

G   S   K   T   I   H   L   T   G   R   S   L   L   P   A   L   E   A   E   P   356
GGCTCGAAGACCATCCACCTCACTGGCCGGTCCCTCCTGCCGGCGCTGGAGGCCGAGCCC           1080
A─────────────────────────────────────────────────────────────────A
```

```
A ──────────────────────────────────────────────────────────── A
  L   W   A   T   V   F   G   S   Q   S   H   H   E   V   T   M   S   Y   P   M    376
CTCTGGGCCACCGTCTTTGGCAGCCAGAGCCACCACGAGGTCACCATGTCCTACCCCATG 1140

R   S   V   Q   H   R   H   F   R   L   V   H   N   L   H   F   K   M   P   F    396
CGCTCCGTGCAGCACCGGCACTTCCGCCTCGTGCACAACCTCAACTTCAAGATGCCCTTT 1200
                                                  *
  P   I   D   Q   D   F   Y   V   S   P   T   F   Q   D   L   L   N   R   T   T    416
CCCATCGACCAGGACTTCTACGTCTCACCCACCTTCCAGGACCTCCTGAACCGCACCACA 1260

A   G   Q   P   T   G   W   Y   K   D   L   R   H   Y   Y   Y   R   A   R   W    436
GCTGGTCAGCCCACGGGCTGGTACAAGGACCTCCGTCATTACTACTACCGGGCGCGCTGG 1320

E   L   Y   D   R   S   R   D   P   H   E   T   Q   N   L   A   T   D   P   R    456
GAGCTCTACGACCGGAGCCGGGACCCCCACGAGACCCAGAACCTGGCCACCGACCCGCGC 1380

F   A   Q   L   L   E   M   L   R   D   Q   L   A   K   W   Q   W   E   T   H    476
TTTGCTCAGCTTCTGGAGATGCTTCGGGACCAGCTGGCCAAGTGGCAGTGGGAGACCCAC 1440

D   P   W   V   C   A   P   D   G   V   L   E   E   K   L   S   P   Q   C   Q    496
GACCCCTGGGTGTGCGCCCCCGACGGCGTCCTGGAGGAGAAGCTCTCTCCCCAGTGCCAG 1500

P   L   H   N   E   L   *                                                        502
CCCCTCCACAATGAGCTGTGACCATCCCAGGAGGCCTGTGCACACATCCCAGGCATGTCC 1560
CAGACACATCCCACACGTGTCCGTGTGGCCGGCCAGCCTGGGGAGTAGTGGCAACAGCCC 1620
TTCCGTCCACACTCCCATCCAAGGAGGGTTCTTCCTTCCTGTGGGTCACTCTTGCCATT 1680
GCCTGGAGGGGGACCAGAGCATGTGACCAGAGCATGTGCCCAGCCCCTCCACCACCAGGG 1740
GCACTGCCGTCATGGCAGGGGACACAGTTGTCCTTGTGTCTGAACCATGTCCCAGCACGG 1800
GAATTCTAGACATACGTGGTCTGCGGACAGGGCAGCGCCCCAGCCCATGACAAGGGAGT 1860
CTTGTTTTCTGGCTTGGTTTGGGGACCTGCAAATGGGAGGCCTGAGGCCCTCTTCAGGCT 1920
TTGGCAGCCACAGATACTTCTGAACCCTTCACAGAGAGCAGGCAGGGGCTTCGGTGCCGC 1980
GTGGGCAGTACGCAGGTCCCACCGACACTCACCTGGGAGCACGGCGCCTGGCTCTTACCA 2040
GCGTCTGGCCTAGAGGAAGCCTTTGAGCGACCTTTGGGCAGGTTTCTGCTTCTTCTGTTT 2100
TGCCCATGGTCAAGTCCCTGTTCCCCAGGCAGGTTTCAGCTGATTGGCAGCAGGCTCCCT 2160
GAGTGATGAGCTTGAACCTGTGGTGTTTCTGGGCAGAAGCTTATCTTTTTTGAGAGTGTC 2220
CGAAGATGAAGGCATGGCGATGCCCGTCCTCTGGCTTGGGTTAATTCTTCGGTGACACTG 2280
GCATTGCTGGGTGGTGATGCCCGTCCTCTGGCTTGGGTTAATTCTTCGGTGACACTGGCG 2340
TTGCTGGGTGGCAATGCCCGTCCTCTGGCTTGGGTTAATTCTTCGGTGACACTGGCGTTG 2400
CTGGGTGGCGATGCCCGTCCTCTGGCTTGGGTTAATTCTTGGATGACGTCGGCGTTGCTG 2460
GGAGAATGTGCCGTTCCTGCCCTGCCTCCACCCACCTCGGGAGCAGAAGCCCGGCCTGGA 2520
CACCCCTCGGCCTGGACACCCCTCGAAGGAGAGGGCGCTTCCTTGAGTAGGTGGGCTCCC 2580
CTTGCCCTTCCCTCCCTATCACTCCATACTGGGGTGGGCTGGAGGAGGCCACAGGCCAGC 2640
TATTGTAAAAGCTTTTTT 2657
```

FIG. 2B

SYNTHETIC MAMMALIAN SULPHAMIDASE AND GENETIC SEQUENCES ENCODING SAME

CROSS REFERENCE TO RELATED APPLICATION

The present application is a continuation of application Ser. No. 08/874,763, filed on Jun. 13, 1997 now U.S. Pat. No. 5,972,333, which is a divisional of application Ser. No. 08/424,881, filed on Apr. 19, 1995 now U.S. Pat. No. 5,863,782.

FIELD OF INVENTION

The present invention relates generally to mammalian sulphamidase and to genetic sequences encoding same and to the use of these in the investigation, diagnosis and treatment of subjects suspected of or suffering from sulphamidase deficiency.

Bibliographic details of the publications referred to by author in this specification are collected at the end of the description. Sequence Identity Numbers (SEQ ID NOs.) for the nucleotide and amino acid sequences referred to in the specification are defined following the bibliography.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

BACKGROUND TO THE INVENTION

The increasing sophistication of recombinant DNA technology is greatly facilitating the efficacy of many commercially important industries including areas of medical and pharmaceutical research and development. The ability to purify native proteins and subsequently clone genetic sequences encoding these proteins is an important first step in the development of a range of therapeutic and diagnostic procedures. However, practitioners have faced many difficulties in purifying target molecules to an extent sufficient to determine amino acid sequences to permit the development of oligonucleotide probes to assist in the cloning of genetic sequences encoding the target molecules.

Such difficulties have been particularly faced in the research and development of lysosomal enzymes. An important lysosomal enzyme is sulphamidase (sulphamate sulphohydrolase EC 3.10.11). This enzyme acts as a exosulphatase in lysosomes to hydrolyse the sulphate ester bond in 2-sulphaminoglucosamine residues present in heparan sulphate and heparin (Hopwood, 1989). A deficiency in this lysosomal hydrolase is responsible for the pathogenesis of Sanfilippo A (Mucopolysaccharidosis type IIIA [MPS-IIIA3]) syndrome (Kresse, 1973; Matalon and Dorfman, 1974). This is an autosomal recessive disorder of glycosaminoglycan catabolism leading to storage and excretion of excessive amounts of heparan sulphate and a variety of clinical phenotypes, but classically presenting with progressive mental retardation in conjunction with skeletal deformities (McKusick and Neufield, 1983).

There is a need, therefore, to purify sulphamidase and to clone genetic sequences encoding same to permit development of a range of therapeutic and diagnostic procedures to assist in the diagnosis and treatment of disease conditions arising from sulphamidase deficiency.

SUMMARY OF THE INVENTION

One aspect of the invention provides an isolated nucleic acid molecule comprising a sequence of nucleotides which encodes or is complementary to a sequence which encodes a mammalian sulphamidase or fragment or derivative thereof.

Another aspect of the invention is directed to an isolated nucleic acid molecule having a nucleotide sequence substantially as set forth in SEQ ID NO:1 or having at least 40% similarity to all or part thereof.

Yet another aspect of the present invention contemplates a recombinant mammalian sulphamidase or fragment or derivative thereof.

Still yet another aspect of the present invention provides a nucleic acid molecule comprising a sequence of nucleotides encoding or complementary to a sequence encoding a polypeptide capable of hydrolysing the sulphate ester bond in 2-sulphaminoglucosamine residues and wherein said nucleotide sequence is capable of hybridising under low stringency conditions to the nucleotide sequence set forth in FIG. 2 (SEQ ID NO:1).

Still another aspect of the present invention is directed to a polypeptide comprising a sequence of amino acids corresponding to the amino sequence set forth in FIG. 2 (SEQ ID NO:2) or having at least 40% similarity thereto, more preferably at least 60% similarity thereto and still more preferably at least 80% or 85–90% similarity thereto or encoded by the nucleotide sequence set forth in FIG. 2 (SEQ ID NO:1) or a nucleotide sequence capable of hybridising to SEQ ID NO:1 under low, preferably under medium and more preferably under high stringent conditions.

In still yet another aspect of the present invention there is contemplated a method for treating a patient suffering from sulphamidase deficiency said method comprising administering to said patient an effective amount of recombinant mammalian sulphamidase or an active fragment or derivative thereof.

Another aspect of the present invention is directed to a pharmaceutical composition comprising a recombinant mammalian sulphamidase or an active fragment or derivative thereof and one or more pharmaceutically acceptable carriers and/or diluents.

BRIEF DESCRIPTION OF THE FIGURES

FIGS. 2A and 2B, when joined at the match line, are a representation of the nucleotide sequence and corresponding amino acid sequence in single letter code of human sulphamidase. * potential N-glycosylation site; ♥ probable of signal peptide peptidase cleavage between amino acids 20 and 21.

Figure 1:
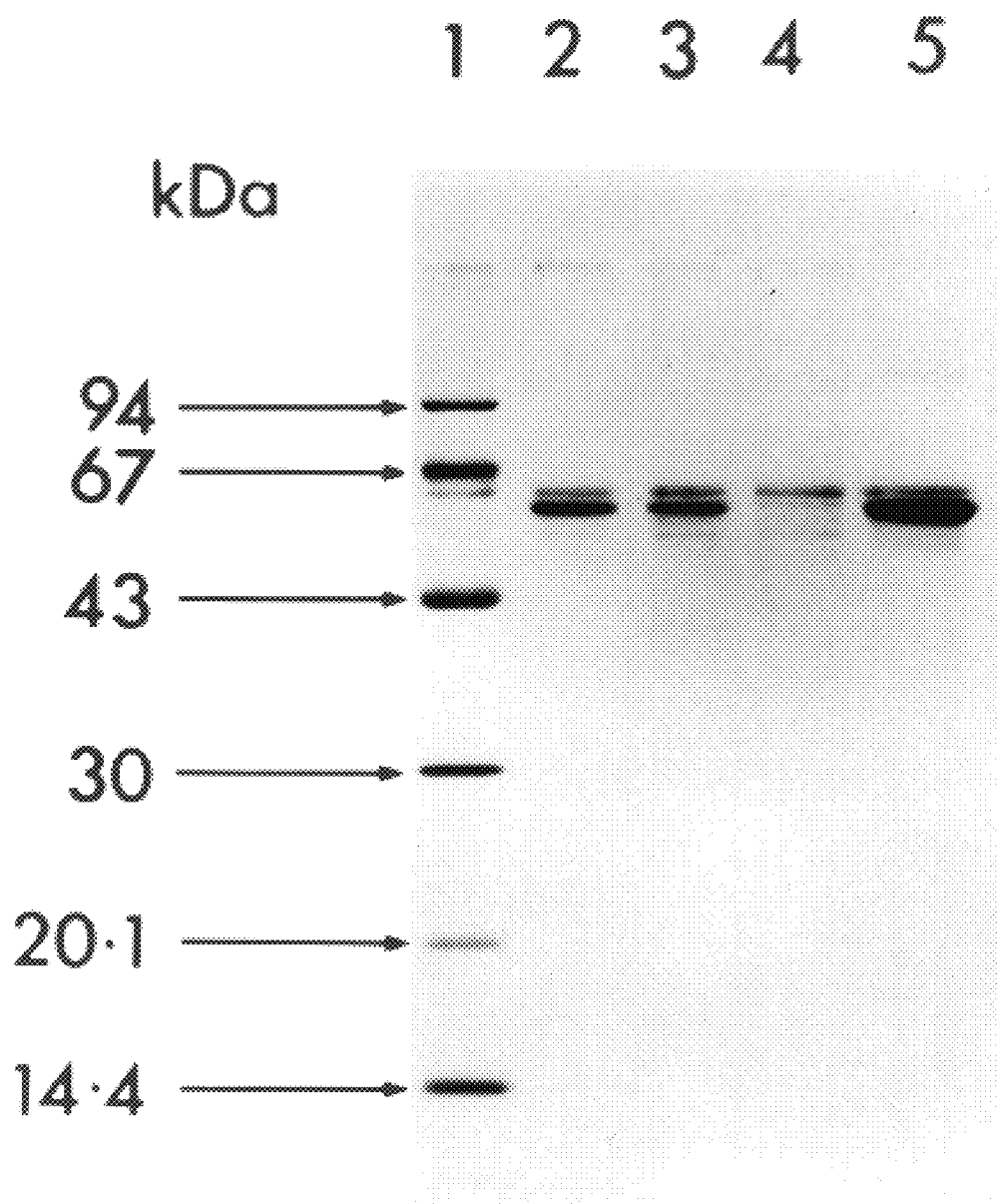
FIG. 1 is a photographic representation of sulphamidase purified from liver, kidney and placenta following SDS/PAGE, Lane 1: $M_r$ standards (kDa); Lanes 2,3 and 5: Purified sulphamidase from human liver, kidney and placenta, respectively, Lane 4: 16

The following single and three letter abbreviations are used for amino acid residues:

| Amino Acid | Three-letter Abbreviation | One-letter Symbol |
| --- | --- | --- |
| Alanine | Ala | A |
| Arginine | Arg | R |
| Asparagine | Asn | N |
| Aspartic acid | Asp | D |
| Cysteine | Cys | C |

-continued

| Amino Acid | Three-letter Abbreviation | One-letter Symbol |
|---|---|---|
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Scr | S |
| Threonine | Thr | T |
| Tryptophan | Trp | W |
| Tyrosine | Tyr | Y |
| Valine | Val | V |
| Any residue | Xaa | X |

DETAILED DESCRIPTION OF THE PREFERRED EMBODIMENTS

The present invention provides an isolated nucleic acid molecule comprising a sequence of nucleotides which encodes, or are complementary to a sequence which encodes, a mammalian sulphamidase or fragment to derivative thereof or its like molecule.

Preferably, the mammalian is a human, livestock animal, companion animal, wild animal or laboratory test animal (e.g. rabbit, rat, mouse or guinea pig). Most preferably, the mammal is a human. Conveniently, the sulphamidase is isolatable from the liver, kidney or placenta. However, the present invention extends to all mammalian sulphamidase enzymes and from any anatomical or cellular source and/or any biological fluid source, such as but not limited to plasma, serum, cell extract or lymph fluid.

Although a preferred embodiment of the present invention contemplates the use of human sulphamidase or genomic or recombinant (e.g. cDNA) genetic sequences encoding same in the investigation, diagnosis and/or treatment of human subjects (i.e. homologous system), one skilled in the art will appreciate that the enzyme or genetic sequences encoding same from a non-human animal may also be useful. Such a heterologous system is encompassed by the present invention.

The "nucleic acid molecule" of the present invention may be RNA or DNA (eg. cDNA), single or double stranded and linear or covalently closed. The nucleic acid molecule may also be genomic DNA corresponding to the entire gene or a substantial portion thereof or to fragments and derivatives thereof. The nucleotide sequence may correspond to the naturally occurring nucleotide sequence or may contain single or multiple nucleotide substitutions, deletions and/or additions. All such modifications encode the sulphamidase-like molecules contemplated by the present invention. The length of the nucleotide sequence may vary from a few bases, such as in nucleic acid probes or primers, to a full length sequence.

The nucleic acid molecule of the present invention may constitute solely the nucleotide sequence encoding sulphamidase or like molecule or may be part of a larger nucleic acid molecule and extends to the genomic clone of sulphamidase. The non-sulphamidase encoding sequences in a larger nucleic acid molecule may include vector, promoter, terminator, enhancer, replication or signal sequences to non-coding regions of a genomic clone.

The present invention is particularly directed to the nucleic acid in cDNA form and particularly when inserted into an expression vector. The expression vector may be replicable in a eukaryotic or prokaryotic cell and may either produce mRNA or the mRNA may be subsequently translated into sulphamidase or like molecule. Particularly preferred eukaryotic cells include CHO cells but may be in any other suitable mammalian cells or cell lines or non-mammalian cells such as yeast or insect cells.

The present invention is further directed to synthetic sulphamidase or like molecule. The term "synthetic" includes recombinant forms and molecules produced by the sequential addition of amino acid residues, or groups of amino acid residues, in defined order. In a most preferred embodiment, the invention relates to recombinant sulphamidase or like molecule encoded by or expressed from the nucleic acid molecules as hereinbefore described.

The synthetic or recombinant sulphamidase may comprise an amino acid sequence corresponding to the naturally occurring amino acid sequence or may contain single or multiple amino acid substitutions, deletions and/or additions. The length of the amino acid sequence may range from a few residues to a full length molecule. Accordingly, this aspect of the present invention contemplates a proteinaceous molecule comprising an amino acid sequence corresponding to the full length mammalian sulphamidase enzyme or to a like molecule. The like molecule, therefore, comprises parts, derivatives and/or portions of the sulphamidase enzyme whether functional or not. Preferably, the mammal is human but may be of non-human origin as contemplated above.

Advantageously, the recombinant sulphamidase is a biologically pure preparation meaning that it has undergone some purification away for other proteins and/or non-proteinacous material. The purity of the preparation may be represented as at least 40% of the enzyme, preferably at least 60%, more preferably at least 75%, even more preferably at least 85% and still more preferably at least 95% relative to non-sulphamidase material as determined by weight, activity, amino acid homology or similarity, antibody reactivity or other convenient means.

Amino acid insertional derivatives of sulphamidase of the present invention include amino and/or carboxyl terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one residue in the sequence has been removed and a different residue inserted in its place. Typical substitutions are those made in accordance with the following Table1:

TABLE 1

Suitable residues for amino acid substitutions

| Original Residue | Exemplary Substitutions |
|---|---|
| Ala | Ser |
| Arg | Lys |
| Asn | Gln; His |
| Asp | Glu |
| Cys | Ser |
| Gln | Asn |

TABLE 1-continued

Suitable residues for amino acid substitutions

| Original Residue | Exemplary Substitutions |
|---|---|
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

When the enzyme is derivatised by amino acid substitution, the amino acids are generally replaced by other amino acids having like properties such as hydrophobicity, hydrophilicity, electronegativity, bulky side chains and the like. Amino acid substitutions are typically of single residues. Amino acid insertions will usually be in the order of about 1–10 amino acid residues and deletions will range from about 1–20 residues. Preferably, deletions or insertions are made in adjacent pairs, i.e. a deletion of two residues or insertion of two residues.

The amino acid variants referred to above may readily be made using peptide synthetic techniques well known in the art, such as solid phase peptide synthesis (Merrified synthesis) and the like, or by recombinant DNA manipulations. Techniques for making substitution mutations at predetermined sites in DNA having known or partially known sequence are well known and include, for example, M13 mutagenesis. The manipulation of DNA sequence to produce variant proteins which manifest as substitutional, insertional or deletional variants are conveniently elsewhere described such as Sambrook et al, 198 *Molecular Cloning: A Laboratory Manual* Cold Spring Harbor Laboratories, Cold Spring Harbor, N.Y.

The derivatives or like molecules include single or multiple substitutions, deletions and/or additions of any component(s) naturally or artificially associated with the sulphamidase enzyme such as carbohydrate, lipid and/or other proteinaceous moieties. For example, the present invention extends to glycosylated and non-glycosylated forms of the molecule. All such molecules are encompassed by the expression "mutants", "derivatives", "fragments", "portions" and "like" molecules. These molecules may be active or non-active and may contain specific regions, such as a catalytic region. Particularly, preferred derivative molecules include those with altered glycosylation patterns relative to the naturally occurring molecule. Even more particularly, the recombinant molecule is more highly glycosylated than the naturally occurring molecule. Such higly glycosylated derivatives have improved take-up properties and enhanced half-lives.

The present invention also extends to synthetic sulphamidase or like molecules when fused to other proteinaceous molecules. The latter may include another enzyme, reporter molecule, purification site or an amino acid sequence which facilitates transport of the molecule out of a cell, such as a signal sequence.

In a most preferred embodiment, the present invention has an amino acid or corresponding sulphamidase cDNA nucleotide sequence substantially as setforth in FIG. 2 having at least 40% similarity, preferably at least 60% similarity thereto or more preferably at least 80% or 85–90% similarity thereto.

In a related embodiment, the present invention provides a nucleic acid molecule comprising a sequence of nucleotides encoding or complementary to a sequence encoding a polypeptide capable of hydrolysing the sulphate ester bond in 2-sulphaminoglucosamine residues and wherein said nucleotide sequence is capable of hybridising under low stringency conditions to the nucleotide sequence set forth in FIG. 2 (SEQ ID NO:1). Preferably, hybridisation is possible under medium stringent conditions, more preferably, hybridisation is possible under high stringent conditions.

For the purposes of defining the level of stringency, reference can conveniently be made to Maniatis et al (1982) at pages 387–389 which is herein incorporated by reference where the washing steps disclosed are considered high stringency. A low stringency is defined herein as being in 4–6X, SSC/0.1–0.5% w/v SDS at 37–45° C. for 2–3 hours. Depending on the source and concentration of nucleic acid involved in the hybridisation, alternative conditions of stringency may be employed such as medium stringent conditions which are considered herein to be 1–4X SSC/0.25–0.5% w/v SDS at $\geq$45° C. for 2–3 hours or high stringent conditions considered herein to be 0.1–1X SSC/0.1% w/v SDS at 60° C. for 1–3 hours.

In a further related embodiment, the present invention contemplates a polypeptide comprising a sequence of amino acids corresponding to the amino sequence set forth in FIG. 2 (SEQ ID NO:2) or having at least 40% similarity thereto, more preferably at least 60% similarity thereto and still more preferably at least 80% or 85–90% similarity thereof or encoded by the nucleotide sequence set forth in FIG. 2 (SEQ ID NO:1) or a nucleotide sequence capable of hybridising to SEQ ID NO:1 under low, preferably under medium and more preferably under high stringent conditions.

The present invention extends to post-transitional modifications to the sulphamidase enzyme. The modifications may be made to the naturally occurring enzyme or following synthesis by recombinant techniques. The modifications may be at the structural level or at, for example, the electrochemical level such as modifying net charge or structural conformation of the enzyme.

Such modification may be important to facilitate entry or penetration of the enzyme into selected tissues such as cartilage or blood brain barriers or to increase circulation half-life.

Such chemically or electrochemically modified ICAM-1-like peptides are referred to herein as "analogues" and are included with the term "derivatives".

Analogues of sulphamidase contemplated herein include, but are not limited to, modifications to side chains, incorporation of unnatural amino acids and/or their derivatives during peptide synthesis and the use of crosslinkers and other methods which impose conformation constraints on the enzyme.

Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5'-phosphate followed by reduction with NaBH$_4$.

The guanidino group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivatives, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuric-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tryosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenypentaoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Crosslinkers can be used, for example, to stabilise 3D conformations, using homo-bifunctional crosslinkers such as the bifunctional imido esters having $(CH_2)_n$ spacer groups with n=1 to n=6, glutaraldehye, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, the enzyme could be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

Electrochemical modifications of sulphamidase include interaction with polylysine or polyethylene glycol or other agent which effects an overall change to the net charge of the enzyme.

The present invention further contemplates antibodies to sulphamidase and preferably synthetic sulphamidase or like molecule. The antibodies may be polyclonal or monoclona, naturally occurring or synthetic (including recombinant, fragment or fusion forms). Such antibodies will be useful in developing immunoassays for sulphamidase.

A further aspect of the present invention contemplates a method of screening for abberations in the sulphamidase gene. Such a method may be accomplished in a number of ways including isolating a source of DNA to be tested or mRNA therefrom and hybridising thereto a nucleic acid molecule as hereinbefore described. Generally, the nucleic acid is probe or primer size and polymerase chain reaction is a convenient means by which to analyse the RNA or DNA. Other suitable assays include the ligation chain reaction and the strand displacement amplification methods. The sulphamidase sequence can also be determined and compared to the naturally occurring sequence. Such methods may be useful in adults and children and may be adapted for a pre-natal test. The DNA to be tested includes a genomic sample carrying the sulphamidase gene, a cDNA clone and/or amplification product.

In accordance with this aspect of the present invention there is provide a method for screening for abberations in the sulphamidase gene including the absence if such a gene or a portion or a substantial portion thereof comprising isolating a sample of DNA or mRNA corresponding to a region of said DNA and contacting same with an oligonucleotide probe capable of hybridising to one or more complementary sequences within the sulphamidase gene and then detecting the hybridastion, the exten of hybridisation or the absence of hybridisation, Alternatively, the probe is a primer and capable of directing amplification of one or more regions of said sulphamidase gene and the amplification products and/or profile of amplification products is compared to an individual carrying the full gene or to reference date base. Conveniently, the amplification products are sequenced to determine the presence or absence of the full gene.

The present invention further extends to a method of treating patients suffering from sulphamidase deficiency, such as in MPS-IIIA, said method comprising administering to said patient an effective amount of sulphamidase or active like form thereof. Preferably, the sulphamidase is in recombinant form. Such a method is referred to as "enzyme therapy". Alternatively, gene therapy can be employed including introducing an active gene (i.e. a nucleic acid molecule as hereinbefore described) or to parts of the gene or other sequences which facilitate expression of a naturally occurring sulphamidase gene.

Administration of the sulphamidase for enzyme therapy may be oral, intravenous, suppository, intraperitoneal, intramuscular, intranasal, intradermal or subcutaneous administration or by infusion or implantation. The sulphamidase is preferably as hereinbefore described including active mutants or derivatives thereof and glycosylation variants thereof. Administration may also be by way of gene therapy including expression of the gene by inclusion of the gene in viral vectors which are introduced into the animal (e.g. human) host to be treated. Alternatively, the gene may be expressed in a bacterial host which is then introduced and becomes part of the bacterial flora in the animal to be tested.

Still yet another aspect of the present invention is directed to a pharmaceutical composition comprising synthetic (e.g. recombinant) sulphamidase or like molecule, including active derivatives and fragments thereof, alone or in combination with other active molecules. Such other molecules may act synergistically with the enzyme or facilitates its entry to a target cell. The composition will also contain one or more pharmaceutically acceptable carriers and/or diluents. The composition may alternatively comprise a genetic component useful in gene therapy.

The active ingredient of the pharmaceutical composition comprising the synetic or recombinant sulphamidase or mutants or fragments or derivatives thereof are contemplated to exhibit excellent activity in treating patients with a deficiency in the enzyme when administered in an amount which depends on the particular case. The variation depends, for example, on the patient and the sulphamidase used. For example, from about 0.5 ug to about 20 mg of enzyme per animal body or, depending on the animal and other factors, per kilogram of body weight may be administered. Dosage regima may be adjusted to provide the optimum therapeutic response. For example, several divided doses may be administered daily, weekly, monthly or in other suitable time intervals or the dose may be proportionally reduced as indicated by the exigencies of the situation. Accordingly, alternative dosages in the order of 1.0 $\mu$g to 15 mg, 2.0 $\mu$g to 10 mg or 10 $\mu$g to 5 mg may be administered in a single or as part of multiple doses. The active compound may be administered in a convenient manner such as by the oral, intravenous (where water soluble), intramuscular, subcutaneous, intranasal, intradermal or suppository routes or implanting (eg using slow release molecules). Depending on the route of administration, the active ingredients which comprise a synthetic (e.g. recombinant) sulphamidase or fragments, derivatives or mutants thereof may be required to be coated in a material to protect same from the action of enzymes, acids and other natural conditions which may inactivate said ingredients. For example, the low lipophilicity of sulphamidase will allow it to be destroyed in the gastrointestinal tract by enzymes capable of cleaving peptide bonds and in the stomach by acid hydrolysis. In order to administer the vaccine by other than parenteral administration, the enzyme will be coated by, or administered with, a material to prevent its inactivation. For example, the enzyme may be administered in an adjuvant, co-administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Conveniently, the adjuvant is Freund's Complete or Incomplete Adjuvant. Enzyme inhibitors include pancreatic trypsin inhibitor, diisopropylfluorophosphate (DEP) and trasylol. Liposomes include water-in-oil-in-water emulsions as well as conventional liposomes.

The active compound may also be administered in dispersions prepared in glycerol, liquid polyethylene glycols, and/or mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, parabens, chlorobutanol, phenol, sorbic acid, thirmerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient(s) into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the sulphamidase of the present invention is suitably protected as described above, the composition may be orally administered, for example, with an inert diluent or with as assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conventiently be between about 5 to about 80% of the weight of the unit. The amount of active compound in the vaccine compositions is such that a suitable dosage will be obtained. Preferred compositions or preparations according to the present invention are prepared, so that an oral dosage unit form contains between about 0.5 ug and 20 mg of active compound.

The tablets, troches, pills, capsules and the like may also contain the following: a binder such as gum gragacanth, acacia, corn starch or gelatin; excipients such as dicalcium phosphate; a distintegrating agent such as corn starch, potato starch, alginic acid and the like; a lubricant such as magnesium stearate; and a sweetening agent such a sucrose, lactose or saccharin may be added or a flavoring agent such as peppermint, oil of wintergreen, or cherry flavouring. When the dosage unit form is a capsule, it may contain, in addition to material of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatves, a dye and flavoring such as cherry or orange flavor. Of course, any material used in preparing any dosage unit form should be pharmaceutically pure and substantially non-toxic in the amounts employed. In addition, the active compound may be incorporated into sustained-release reparations and formulations.

As used herein "pharmaceutically acceptable carriers and/or diluents" include any and all solents, dispersion media, aqueous solutions, coatings, antibacterial and antifungal agents, isotonic and absorption delaying agents, and the like. The use of such media and agents for pharmaceutical active substances is well known in the art. Except insofar as any conventional media or agent is incompatible with the active ingredient, use thereof in the pharmaceutical compositions is contemplated. Supplementary active ingredients can also be incorporated into the compositions.

The present invention further relates to the use of sulphamidase or active fragment, mutant or derivative thereof in the manufacture of a medicament for the treatment of patients suffering from a deficiency in the naturally occurring enzyme (e.g. MPS-IIIA).

The present invention is further described with reference to the following non-limiting examples.

EXAMPLE 1

Purification of Sulphamidase

Sulphamidases were purified according to the method described n Freeman and Hopwood (1986). Enzymes were purified to homogenicty from human liver, kidney and placenta. Evidence of purity is shown following SDS/PAGE which is represented in FIG. 1. All samples were reduced with dithiothreitol prior to electrophoresis.

EXAMPLE 2

Characterisation of Sulphamidase

Results presented in FIG. 1 show a subunit of about $M_r$ 56,000 from sulphamidase purified from human liver, kidney and placenta. The native $M_r$ is about 100,000 to 120,000.

EXAMPLE 3

N-Terminal Amino Acid Sequence Determination

The N-terminal amino acid sequence was determined using the methods of Clements et al (1989) and Wilson et al (1990).

The amino acid sequence is shown in Table 2.

EXAMPLE 4

Cloning of Sulphamidase cDNA

The N-terminal amino acid sequence (Example 3) was used to generate oligonucleotides and primers to screen a human kidney cDNA library. An approximately 2.7 kbp cDNA clone was then isolated encoding the entire sequence of human sulphamidase. The nucleotide sequence (SEQ ID NO:1) and corresponding amino acid sequence (SEQ ID NO:2) are shown in FIG. 2.

The amino acid sequence is shown in single letter code above the cDNA sequence. Nucleotide and amino acid numbers are in the right margin. The probable site of signal peptide peptidase cleavage between amino acids 20 and 21 is shown by an arrow. Amino acids colinear with the amino-terminal peptide data is underlined. The five potential N-glycosylation sites are asterisked above the peptide sequence. The open reading frame is 1506 nucleotides long and encodes a 502 amino acid protein. The predicted molecular mass of the mature protein (minus the 20 amino acid signal peptide) is about 54,679 kilo daltons.

TABLE 2

N-Terminal amino acid sequence (SEQ ID NO:3) determined from purified human liver sulphamidase

R P R N A L L L L A D D O G F E S G A Y X[1] N S A I

X[1]no residue could be identified for this position, indicating that this residue could be phosphorylated or glycosylated. It is likely to be N-glycosylated because it would be a consensus sequence [N x T(s)] for N-glycosylation.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

---

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 2657 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: CDS
      (B) LOCATION: 13..1518

(xi) SEQUENCE DESCRIPTION: SEQ ID NO: 1:

GAATTCCGGG CC ATG AGC TGC CCC GTG CCC GCC TGC TGC GCG CTG CTG    48

```
            Met Ser Cys Pro Val Pro Ala Cys Cys Ala Leu Leu
              1               5                  10

CTA GTC CTG GGG CTC TGC CGG GCG CGT CCC CGG AAC GCA CTG CTG CTC      96
Leu Val Leu Gly Leu Cys Arg Ala Arg Pro Arg Asn Ala Leu Leu Leu
         15                  20                  25

CTC GCG GAT GAC GGA GGC TTT GAG AGT GGC GCG TAC AAC AAC AGC GCC     144
Leu Ala Asp Asp Gly Gly Phe Glu Ser Gly Ala Tyr Asn Asn Ser Ala
         30                  35                  40

ATC GCC ACC CCG CAC CTG GAC GCC TTG GCC CGC CGC AGC CTC CTC TTT     192
Ile Ala Thr Pro His Leu Asp Ala Leu Ala Arg Arg Ser Leu Leu Phe
 45              50                  55                      60

CGC AAT GCC TTC ACC TCG GTC AGC AGC TGC TCT CCC AGC CGC GCC AGC     240
Arg Asn Ala Phe Thr Ser Val Ser Ser Cys Ser Pro Ser Arg Ala Ser
                 65                  70                  75

CTC CTC ACT GGC CTG CCC CAG CAT CAG AAT GGG ATG TAC GGG CTG CAC     288
Leu Leu Thr Gly Leu Pro Gln His Gln Asn Gly Met Tyr Gly Leu His
             80                  85                  90

CAG GAC GTG CAC CAC TTC AAC TCC TTC GAC AAG GTG CGG AGC CTG CCG     336
Gln Asp Val His His Phe Asn Ser Phe Asp Lys Val Arg Ser Leu Pro
         95                 100                 105

CTG CTG CTC AGC CAA GCT GGT GTG CGC ACA GGC ATC ATC GGG AAG AAG     384
Leu Leu Leu Ser Gln Ala Gly Val Arg Thr Gly Ile Ile Gly Lys Lys
    110                 115                 120

CAC GTG GGG CCG GAG ACC GTG TAC CCG TTT GAC TTT GCG TAC ACG GAG     432
His Val Gly Pro Glu Thr Val Tyr Pro Phe Asp Phe Ala Tyr Thr Glu
125                 130                 135                 140

GAG AAT GGC TCC GTC CTC CAG GTG GGG CGG AAC ATC ACT AGA ATT AAG     480
Glu Asn Gly Ser Val Leu Gln Val Gly Arg Asn Ile Thr Arg Ile Lys
                145                 150                 155

CTG CTC GTC CGG AAA TTC CTG CAG ACT CAG GAT GAC CGG CCT TTC TTC     528
Leu Leu Val Arg Lys Phe Leu Gln Thr Gln Asp Asp Arg Pro Phe Phe
            160                 165                 170

CTC TAC GTC GCC TTC CAC GAC CCC CAC CGC TGT GGG CAC TCC CAG CCC     576
Leu Tyr Val Ala Phe His Asp Pro His Arg Cys Gly His Ser Gln Pro
        175                 180                 185

CAG TAC GGA ACC TTC TGT GAG AAG TTT GGC AAC GGA GAG AGC GGC ATG     624
Gln Tyr Gly Thr Phe Cys Glu Lys Phe Gly Asn Gly Glu Ser Gly Met
    190                 195                 200

GGT CGT ATC CCA GAC TGG ACC CCC CAG GCC TAC GAC CCA CTG GAC GTG     672
Gly Arg Ile Pro Asp Trp Thr Pro Gln Ala Tyr Asp Pro Leu Asp Val
205                 210                 215                 220

CTG GTG CCT TAC TTC GTC CCC AAC ACC CCG GCA GCC CGA GCC GAC CTG     720
Leu Val Pro Tyr Phe Val Pro Asn Thr Pro Ala Ala Arg Ala Asp Leu
                225                 230                 235

GCC GCT CAG TAC ACC ACC GTC GGC CGC ATG GAC CAA GGA GTT GGA CTG     768
Ala Ala Gln Tyr Thr Thr Val Gly Arg Met Asp Gln Gly Val Gly Leu
            240                 245                 250

GTG CTC CAG GAG CTG CGT GAC GCC GGT GTC CTG AAC GAC ACA CTG GTG     816
Val Leu Gln Glu Leu Arg Asp Ala Gly Val Leu Asn Asp Thr Leu Val
        255                 260                 265

ATC TTC ACG TCC GAC AAC GGG ATC CCC TTC CCC AGC GGC AGG ACC AAC     864
Ile Phe Thr Ser Asp Asn Gly Ile Pro Phe Pro Ser Gly Arg Thr Asn
    270                 275                 280

CTG TAC TGG CCG GGC ACT GCT GAA CCC TTA CTG GTG TCA TCC CCG GAG     912
Leu Tyr Trp Pro Gly Thr Ala Glu Pro Leu Leu Val Ser Ser Pro Glu
285                 290                 295                 300

CAC CCA AAA CGC TGG GGC CAA GTC AGC GAG GCC TAC GTG AGC CTC CTA     960
His Pro Lys Arg Trp Gly Gln Val Ser Glu Ala Tyr Val Ser Leu Leu
                305                 310                 315
```

```
GAC CTC ACG CCC ACC ATC TTG GAT TGG TTC TCG ATC CCG TAC CCC AGC      1008
Asp Leu Thr Pro Thr Ile Leu Asp Trp Phe Ser Ile Pro Tyr Pro Ser
            320                 325                 330

TAC GCC ATC TTT GGC TCG AAG ACC ATC CAC CTC ACT GGC CGG TCC CTC      1056
Tyr Ala Ile Phe Gly Ser Lys Thr Ile His Leu Thr Gly Arg Ser Leu
        335                 340                 345

CTG CCG GCG CTG GAG GCC GAG CCC CTC TGG GCC ACC GTC TTT GGC AGC      1104
Leu Pro Ala Leu Glu Ala Glu Pro Leu Trp Ala Thr Val Phe Gly Ser
    350                 355                 360

CAG AGC CAC CAC GAG GTC ACC ATG TCC TAC CCC ATG CGC TCC GTG CAG      1152
Gln Ser His His Glu Val Thr Met Ser Tyr Pro Met Arg Ser Val Gln
365                 370                 375                 380

CAC CGG CAC TTC CGC CTC GTG CAC AAC CTC AAC TTC AAG ATG CCC TTT      1200
His Arg His Phe Arg Leu Val His Asn Leu Asn Phe Lys Met Pro Phe
                385                 390                 395

CCC ATC GAC CAG GAC TTC TAC GTC TCA CCC ACC TTC CAG GAC CTC CTG      1248
Pro Ile Asp Gln Asp Phe Tyr Val Ser Pro Thr Phe Gln Asp Leu Leu
            400                 405                 410

AAC CGC ACC ACA GCT GGT CAG CCC ACG GGC TGG TAC AAG GAC CTC CGT      1296
Asn Arg Thr Thr Ala Gly Gln Pro Thr Gly Trp Tyr Lys Asp Leu Arg
        415                 420                 425

CAT TAC TAC TAC CGG GCG CGC TGG GAG CTC TAC GAC CGG AGC CGG GAC      1344
His Tyr Tyr Tyr Arg Ala Arg Trp Glu Leu Tyr Asp Arg Ser Arg Asp
    430                 435                 440

CCC CAC GAG ACC CAG AAC CTG GCC ACC GAC CCG CGC TTT GCT CAG CTT      1392
Pro His Glu Thr Gln Asn Leu Ala Thr Asp Pro Arg Phe Ala Gln Leu
445                 450                 455                 460

CTG GAG ATG CTT CGG GAC CAG CTG GCC AAG TGG CAG TGG GAG ACC CAC      1440
Leu Glu Met Leu Arg Asp Gln Leu Ala Lys Trp Gln Trp Glu Thr His
                465                 470                 475

GAC CCC TGG GTG TGC GCC CCC GAC GGC GTC CTG GAG GAG AAG CTC TCT      1488
Asp Pro Trp Val Cys Ala Pro Asp Gly Val Leu Glu Glu Lys Leu Ser
            480                 485                 490

CCC CAG TGC CAG CCC CTC CAC AAT GAG CTG TGACCATCCC AGGAGGCCTG        1538
Pro Gln Cys Gln Pro Leu His Asn Glu Leu
        495                 500

TGCACACATC CCAGGCATGT CCCAGACACA TCCCACACGT GTCCGTGTGG CCGGCCAG      1598

TGGGGAGTAG TGGCAACAGC CCTTCCGTCC ACACTCCCAT CCAAGGAGGG TTCTTCCT      1658

CTGTGGGGTC ACTCTTGCCA TTGCCTGGAG GGGGACCAGA GCATGTGACC AGAGCATG      1718

CCCAGCCCCT CCACCACCAG GGGCACTGCC GTCATGGCAG GGGACACAGT TGTCCTTG      1778

TCTGAACCAT GTCCCAGCAC GGGAATTCTA GACATACGTG GTCTGCGGAC AGGGCAGC      1838

CCCCAGCCCA TGACAAGGGA GTCTTGTTTT CTGGCTTGGT TTGGGGACCT GCAAATGG      1898

GGCCTGAGGC CCTCTTCAGG CTTTGGCAGC CACAGATACT TCTGAACCCT TCACAGAG      1958

CAGGCAGGGG CTTCGGTGCC GCGTGGGCAG TACGCAGGTC CCACCGACAC TCACCTGG      2018

GCACGGCGCC TGGCTCTTAC CAGCGTCTGG CCTAGAGGAA GCCTTTGAGC GACCTTTG      2078

CAGGTTTCTG CTTCTTCTGT TTTGCCCATG GTCAAGTCCC TGTTCCCCAG GCAGGTTT      2138

GCTGATTGGC AGCAGGCTCC CTGAGTGATG AGCTTGAACC TGTGGTGTTT CTGGGCAG      2198

GCTTATCTTT TTTGAGAGTG TCCGAAGATG AAGGCATGGC GATGCCCGTC CTCTGGCT      2258

GGTTAATTCT TCGGTGACAC TGGCATTGCT GGGTGGTGAT GCCCGTCCTC TGGCTTGG      2318

TAATTCTTCG GTGACACTGG CGTTGCTGGG TGGCAATGCC CGTCCTCTGG CTTGGGTT      2378

TTCTTCGGTG ACACTGGCGT TGCTGGGTGG CGATGCCCGT CCTCTGGCTT GGGTTAAT      2438

TTGGATGACG TCGGCGTTGC TGGGAGAATG TGCCGTTCCT GCCCTGCCTC CACCCACC      2498
```

```
GGGAGCAGAA GCCCGGCCTG GACACCCCTC GGCCTGGACA CCCCTCGAAG GAGAGGGC      2558

TTCCTTGAGT AGGTGGGCTC CCCTTGCCCT TCCCTCCCTA TCACTCCATA CTGGGGTG      2618

CTGGAGGAGG CCACAGGCCA GCTATTGTAA AAGCTTTTT                            2657
```

(2) INFORMATION FOR SEQ ID NO: 2:

(i) SEQUENCE CHARACTERISTICS:
        (A) LENGTH: 502 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ser Cys Pro Val Pro Ala Cys Cys Ala Leu Leu Val Leu Gly
 1               5                  10                  15

Leu Cys Arg Ala Arg Pro Arg Asn Ala Leu Leu Leu Ala Asp Asp
                20                  25                  30

Gly Gly Phe Glu Ser Gly Ala Tyr Asn Asn Ser Ala Ile Ala Thr Pro
            35                  40                  45

His Leu Asp Ala Leu Ala Arg Arg Ser Leu Leu Phe Arg Asn Ala Phe
        50                  55                  60

Thr Ser Val Ser Ser Cys Ser Pro Ser Arg Ala Ser Leu Leu Thr Gly
65                  70                  75                  80

Leu Pro Gln His Gln Asn Gly Met Tyr Gly Leu His Gln Asp Val His
                85                  90                  95

His Phe Asn Ser Phe Asp Lys Val Arg Ser Leu Pro Leu Leu Leu Ser
            100                 105                 110

Gln Ala Gly Val Arg Thr Gly Ile Ile Gly Lys Lys His Val Gly Pro
        115                 120                 125

Glu Thr Val Tyr Pro Phe Asp Phe Ala Tyr Thr Glu Glu Asn Gly Ser
    130                 135                 140

Val Leu Gln Val Gly Arg Asn Ile Thr Arg Ile Lys Leu Leu Val Arg
145                 150                 155                 160

Lys Phe Leu Gln Thr Gln Asp Asp Arg Pro Phe Phe Leu Tyr Val Ala
                165                 170                 175

Phe His Asp Pro His Arg Cys Gly His Ser Gln Pro Gln Tyr Gly Thr
            180                 185                 190

Phe Cys Glu Lys Phe Gly Asn Gly Glu Ser Gly Met Gly Arg Ile Pro
        195                 200                 205

Asp Trp Thr Pro Gln Ala Tyr Asp Pro Leu Asp Val Leu Val Pro Tyr
    210                 215                 220

Phe Val Pro Asn Thr Pro Ala Ala Arg Ala Asp Leu Ala Ala Gln Tyr
225                 230                 235                 240

Thr Thr Val Gly Arg Met Asp Gln Gly Val Gly Leu Val Leu Gln Glu
                245                 250                 255

Leu Arg Asp Ala Gly Val Leu Asn Asp Thr Leu Val Ile Phe Thr Ser
            260                 265                 270

Asp Asn Gly Ile Pro Phe Pro Ser Gly Arg Thr Asn Leu Tyr Trp Pro
        275                 280                 285

Gly Thr Ala Glu Pro Leu Leu Val Ser Ser Pro Glu His Pro Lys Arg
    290                 295                 300

Trp Gly Gln Val Ser Glu Ala Tyr Val Ser Leu Leu Asp Leu Thr Pro
305                 310                 315                 320
```

```
-continued

Thr Ile Leu Asp Trp Phe Ser Ile Pro Tyr Pro Ser Tyr Ala Ile Phe
            325                 330                 335

Gly Ser Lys Thr Ile His Leu Thr Gly Arg Ser Leu Leu Pro Ala Leu
            340                 345                 350

Glu Ala Glu Pro Leu Trp Ala Thr Val Phe Gly Ser Gln Ser His His
        355                 360                 365

Glu Val Thr Met Ser Tyr Pro Met Arg Ser Val Gln His Arg His Phe
    370                 375                 380

Arg Leu Val His Asn Leu Asn Phe Lys Met Pro Phe Pro Ile Asp Gln
385                 390                 395                 400

Asp Phe Tyr Val Ser Pro Thr Phe Gln Asp Leu Leu Asn Arg Thr Thr
            405                 410                 415

Ala Gly Gln Pro Thr Gly Trp Tyr Lys Asp Leu Arg His Tyr Tyr Tyr
            420                 425                 430

Arg Ala Arg Trp Glu Leu Tyr Asp Arg Ser Arg Asp Pro His Glu Thr
            435                 440                 445

Gln Asn Leu Ala Thr Asp Pro Arg Phe Ala Gln Leu Leu Glu Met Leu
        450                 455                 460

Arg Asp Gln Leu Ala Lys Trp Gln Trp Glu Thr His Asp Pro Trp Val
465                 470                 475                 480

Cys Ala Pro Asp Gly Val Leu Glu Glu Lys Leu Ser Pro Gln Cys Gln
            485                 490                 495

Pro Leu His Asn Glu Leu
            500

(2) INFORMATION FOR SEQ ID NO: 3:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Arg Pro Arg Asn Ala Leu Leu Leu Leu Ala Asp Asp Gly Gly Phe Glu
1               5                   10                  15

Ser Gly Ala Tyr Xaa Asn Ser Ala Ile
            20                  25
```

REFERENCES

Clements P R, Brooks D A, McCourt PAG and Hopwood J J (1989) *Biochem. J.* 259: 199–208.

Freeman C and Hopwood J J, (1986) *Biochem. J.* 234: 83–92.

Hopwood J J (1989) In: *"Heparin: Chemical and Biological Properties, Clinical Applications"* (Lane D W and Lindahl U, eds.), 190–229, Edward Arnold, London.

Kresse H (1973) *Biochem. Biophys. Res. Commun.* 54: 1111–1118.

Matalon R and Dorfman A (1974) *J. Clin. Invest.* 54: 907–912.

McKusick V and Neufeld E (1983) In: *"The Metabolic Basis of Inherited Disease"* (Stanbury J B, Wyngaarden J B, Fredrickson D S, Goldsten J L and Brown M S, eds), 5th Ed., 751–771, McGraw-Hill, New York.

Wilson P J, Morris C P, Anson D S, Occhiodor T, Bielicki J, Clements P R and Hopwood J J (1990) *Proc. Natl. Acad. Sci. USA* 87: 8531–8535.

What is claimed is:

1. A purified recombinant sulphamidase wherein the sulphamidase is secreted and purified from mammalian cells in culture transfected with a nucleic acid sequence encoding human sulphamidase and wherein the secreted sulphamidase is substantially in unprocessed form.

2. The purified human sulphamidase according to claim 1 wherein the sulphamidase is full length.

3. The recombinant human sulphamidase according to claim 1 or 2 having an amino acid sequence as set forth in SEQ ID NO:2.

4. A pharmaceutical composition comprising purified recombinant sulphamidase and one or more pharmaceutically acceptable carriers or diluents wherein the sulphamidase is secreted from mammalian cells in culture transfected with a nucleic acid sequence encoding human sulphamidase and wherein the secreted sulphamidase is substantially in unprocessed form.

5. A purified recombinant sulphamidase wherein the sulphamidase is secreted from mammalian cells in culture transfected with a nucliec acid sequence encoding human sulphamidase, wherein the secreted sulphamidase is substantially in unprocessed form and wherein the sulphamidase is chemically modified by interaction with polylysine or polyethylene glycol.

* * * * *